United States Patent [19]

Findlay et al.

[11] Patent Number: 4,639,459

[45] Date of Patent: Jan. 27, 1987

[54] USE OF TRIFLUOROMETHYL COMPOUNDS

[75] Inventors: John W. A. Findlay, Chapel Hill, N.C.; Geoffrey G. Coker, Bromley, England

[73] Assignee: Burroughs Wellcome Co., Research Triangle Park, N.C.

[21] Appl. No.: 771,142

[22] Filed: Aug. 29, 1985

Related U.S. Application Data

[63] Continuation of Ser. No. 462,788, Feb. 1, 1983, abandoned.

[51] Int. Cl.[4] .............................................. A61K 31/44
[52] U.S. Cl. ..................................................... 514/343
[58] Field of Search ......................................... 514/343

[56] References Cited

U.S. PATENT DOCUMENTS

| | | | |
|---|---|---|---|
| 2,567,245 | 9/1951 | Sperber et al. | 260/296 |
| 2,712,023 | 6/1955 | Adamson | 546/194 |
| 3,862,173 | 1/1975 | Carr et al. | 260/240 R |
| 4,355,036 | 10/1982 | Villani | 546/80 |
| 4,501,893 | 2/1985 | Findlay et al. | 546/281 |
| 4,562,258 | 12/1985 | Findlay et al. | 514/343 |
| 4,584,382 | 4/1986 | Findlay et al. | 546/314 |

FOREIGN PATENT DOCUMENTS

| | | |
|---|---|---|
| 1227464 | 10/1966 | Fed. Rep. of Germany . |
| 41061 | 12/1972 | Israel . |
| 807757 | 1/1959 | United Kingdom . |

OTHER PUBLICATIONS

Burger, Medicinal Chemistry, 3rd ed., Part I, p. 76.
Chemical Abstracts, 71: 11415f (1968).
Buzas et al., J. Med. Chem. 1980, 23, 149–153.
Hucker et al., Drug Metabolism and Disposition, vol. 9, No. 5, pp. 428–433 (1981).
ASPET 1980, Abstract, Findlay et al., Pharmacokinetics of Triprolidine in Animals and Man as Measured by a New Radioimmunoassay, Wellcome Research Laboratories, Research Triangle Park, NC 27709.
PDR–1978–ACTIDIL (Triprolidine Hydrochloride) p. 707.
PDR–1978–ACTIFED–c (Expectorant–Tablets & Syrup) p. 708.

Primary Examiner—Albert T. Meyers
Assistant Examiner—John M. Kilcoyne
Attorney, Agent, or Firm—Donald Brown

[57] ABSTRACT

This disclosure describes a compound of Formula 1

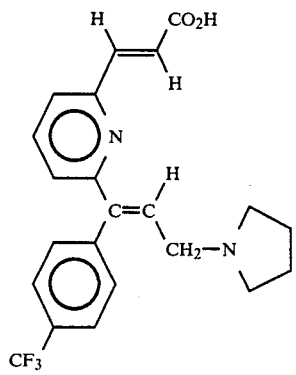

(including its pharmaceutically acceptable salts and esters) which has potent antihistamine activity which is substantially free from sedative effects and which has little or no anticholinergic effects.

4 Claims, No Drawings

USE OF TRIFLUOROMETHYL COMPOUNDS

This application is a continuation of application Ser. No. 462,788, filed 2/1/83, now abandoned.

The present invention relates to a new chemical compound exhibiting antihistamine activity substantially free from sedative effects.

U.S. Pat. No. 2,712,023 discloses a group of pyridyl propenylamines with antihistamine activity, the most outstanding of which is the compound named (E)-1-(4-methylphenyl)-1-(2-pyridyl)-3-pyrrolidinoprop-1-ene and hereinafter referred to by its generic name, triprolidine. Triprolidine has gained widespread clinical acceptance and is one of the most potent antihistamines available. However, like all other potent antihistamines in clinical use it produces sedation and drowsiness in varying degrees in most patients (L. Goodman and A. Gilman, *The Pharmacological Basis of Therapeutics*, 4th ed., p. 640, Macmillan, New York, 1970). This sedating effect limits the use of antihistamines by patients who must operate machinery, drive motor vehicles or must engage in activities requiring mental alertness.

The antihistamines now in use, eg. diphenhydramine, pheniramines, pyrilamine, promethazine and triprolidine, exhibit varying degrees of anticholinergic activity. Such activity causes dryness of mouth, blurred vision and tachycardia and is generally regarded as undesirable.

A novel compound having potent antihistamine activity which is substantially free from sedative effects, and which has little or no anticholinergic effect has now been discovered.

Accordingly this invention provides the compound of formula (I), which is named (E)-3-{6-[3-Pyrrolidino-1(4-Trifluoromethylphenyl)prop-1E-enyl]-2-pyridyl}acrylic acid.

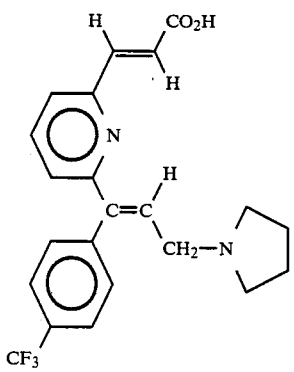

This invention also includes esters (wherein the hydrogen of the carboxylic acid group is replaced by one of the widely known methods of organic chemistry with straight or branched lower alkyls of 1–4 carbons) as well as pharmaceutically acceptable acid addition salts and salts of the carboxylic acid group of the compound of formula (I).

If the acrylic acid side chain is placed in any position on the pyridine ring other than that shown in FIG. 1 (i.e., the 2 position) or the configuration about the central double bond is Z rather than E as shown above, the antihistaminic activity of such a compound is significantly reduced relative to the compound of formula (I).

1. A method for preparing the compound of formula (I) comprises reacting a compound of (II) with the compound of formula (III) by the Wittig method (see *Organic Reactions*, 14, 270–490 (1965) and *Pure and Applied Chemistry*, 9, 245–254 (1964)).

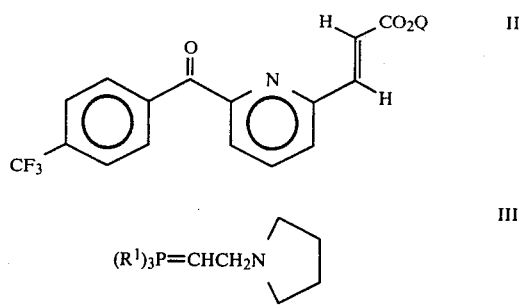

wherein Q is a lower alkyl group (1–4 carbons) or an alkali metal such as lithium or sodium and $R^1$ is aryl such as phenyl or lower alkyl (1 to 4 carbons). The reaction may be followed by deprotection of the carboxyl group as necessary. The product may be converted to an acid addition salt, a salt of the carboxylic acid, an ester or an amide by conventional methods.

The compound of formula (III) is a Wittig reagent which may be prepared by treatment of a phosphonium salt (IV), infra, with a strong base, for example an alkyl or aryl lithium compound or sodium hydride in a suitable solvent, for example toluene or tetrahydrofuran:

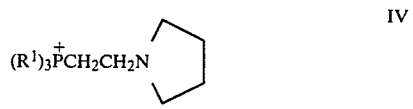

wherein $R^1$ is as defined above. The phosphonium salts (IV) are prepared by known methods (e.g., see British Pat. No. 1,161,201).

Compounds of formula (II) may be prepared by reacting a compound of formula (V) with an acrylate ester (VI) in presence of a catalyst consisting of palladium acetate and a triarylphosphine and a tertiary amine such as triethylamine or tributylamine. Optionally a solvent such as acetonitrile may be used and the reactants may with advantage be heated together in a sealed pressure vessel (e.g., see R. F. Heck et al., *J. Org. Chem.*, 43, 2947 (1978)). Compounds of formula (V) and (VI) are represented by the formulas

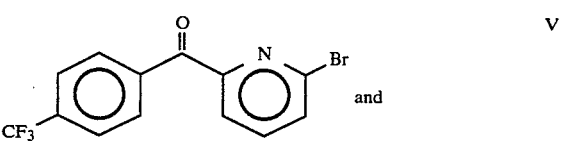

$CH_2=CHCO_2R^2$, respectively, VI wherein $R^2$ is a lower alkyl group (1–4 carbon atoms). Compounds of formula (II) may also be prepared by reacting a compound of formula (VII):

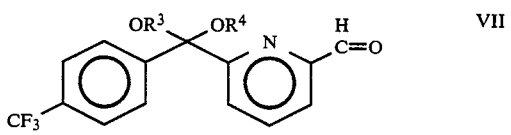

wherein R³ and R⁴ may be the same or different and are lower alkyl, or may together form a cyclic ketal, with malonic acid in the presence of a pyridine and piperidine, or with a Wittig reagent prepared by treating a phosphonium salt (VIII A) or a phosphonate ester (VIII B) with a suitable base in an appropriate solvent:

(R²)₃PCH₂CO₂H    VIIIA

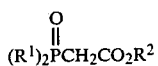

$$\underset{(R^1)_2PCH_2CO_2R^2}{\overset{O}{\underset{\|}{}}} \quad \text{VIIIB}$$

wherein R¹ and R² are as defined above. The ketone (II) is generated by acidic hydrolysis of the protecting ketal.

Compounds of formula (VII) may be prepared from compounds of formula (V) by conversion to a ketal by reaction with a mono or dihydroxy compound in presence of an acid catalyst followed by reaction with a metal alkyl compound for example butyllithium and subsequent treatment with dimethylformamide. The reaction is preferably conducted at low temperature (below −60°) in a solvent such as toluene.

In turn compounds of formula (V) can be prepared by treatment of 2,6-dibromopyridine with a metal alkyl compound, for example butyllithium in a suitable solvent such as toluene, followed by reaction with 4-trifluoromethylbenzonitrile.

2. Compounds of formula (I) may also be synthesized by reacting compounds of formula (IX)

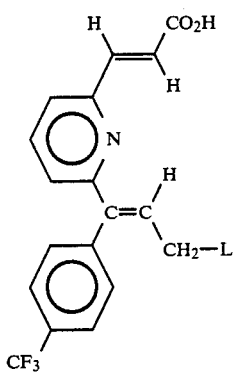

wherein L is a leaving group as defined by J. March, *Advanced Organic Chemistry*, 2nd ed., pages 683 and 895, McGraw Hill, New York, 1977, e.g. —Br, —Cl, toluene sulphonate, etc. with pyrrolidine.

3. A further method for synthesis of compound of formula (I) comprises dehydration of compounds of formula (X).

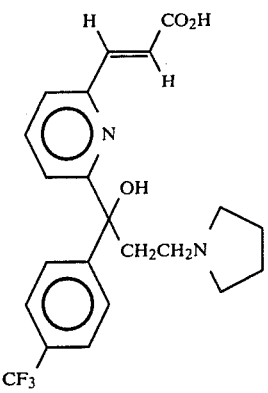

The compound of this invention has the same utilities as an antihistamine used clinically at present. It binds competitively to the H₁ histamine receptor sites (thus blocking the H₁ histamine receptor sites) to reduce the detrimental effects of histamine in mammals including humans and as such may be used to relieve symptoms of nasal stuffiness due to colds and vasomotor rhinitis and for the symptomatic control of all allergic conditions including nasal allergy, perennial rhinitis, urticaria, angioneurotic oedema, allergic conjunctivitis, food allergy, drug and serum reactions, insect bites and stings and desensitizing reactions. The compound is also indicated in all conditions responsive to its antipuritic activity including allergic dermatoses, neurodermatitis, anogenital pruritus, and pruritus of non-specific origin such as eczema, and of specific cause such as chickenpox, photosensitivity and sunburn. In contrast to the antihistamines in present use, the compound of this invention is essentially not sedating and has little or no anticholinergic side effects.

Pharmacokinetic studies comparing the relative distribution in brain and plasma of the compound of this invention, and triprolidine indicate that, unlike triprolidine, this compound does not readily penetrate the brains of rodents.

The amount of active compound (defined herein as the compound of formula (I) including esters and pharmaceutically acceptable salts) required for use in the above conditions will vary both with the route of administration, the condition under treatment and the mammal undergoing treatment, and is ultimately at the discretion of the physician. A suitable oral dose of the active compound for a mammal is in the range of from 0.025 to 1.0 mg per kilogram body weight per day; preferably from 0.04 to 0.24 mg/kg. For example a typical dose for a human recipient of compound (A) is 0.12 mg/kg body weight per day.

The desired daily dose is preferably presented as from one to six sub-doses administered at appropriate intervals throughout the day as needed. Where three sub-doses of compounds of formula (I) are employed, each will preferably lie in the range of from 0.014 to 0.08 mg/kg body weight; for example, a typical unit sub-dose (which can be given in a pharmaceutical formulation such as a tablet or a capsule) of the active compound for a human recipient is about 0.25 to 20 mg, typically 2 mg, while the typical total daily preferred dose is in the range of 2 to 12 mg. As a syrup the amount would be at a concentration of 0.25 to 20 mg/5 mL of solvent, e.g., water, flavoring, etc.

While it is possible for the active compound previously described to be administered alone as the raw chemical, it is preferable to present the active compound, a compound of formula (I), as a pharmaceutical formulation. Formulations of the present invention, both for veterinary and for human medical use, comprise the active compound together with one or more pharmaceutically acceptable carriers thereof and optionally any other therapeutic ingredients. For example, the active compound may be formulated with a sympathomimetic agent such as the decongestants pseudoephedrine or phenylpropanolamine, an antitussive such as codeine, an analgesic such as acetaminophen, an antiinflammatory and antipyretic such as aspirin, or an expectorant such as guaifenesin. The carrier(s) must be pharmaceutically acceptable in the sense of being compatible with the other ingredients of the formulation and not deleterious to the recipient thereof. The formulations include those suitable for oral, rectal, topical, nasal, opthalmic or parenteral (including subcutaneous, intramuscular and intravenous) administration.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier or both and then, if necessary, shaping the product into the desired formulations.

Formulations of the present invention suitable for oral administration may be presented as discrete units such as capsules, cachets, tablets or lozenges, each containing a predetermined amount of the active compound (defined herein as a compound of formula (I)); as a powder or granules; or a suspension in an aqueous liquid or non-aqueous liquid such as a syrup, an elixir, an emulsion or a draught.

A tablet may be made by compression or molding, optionally with one or more accessory ingredients. Compressed tablets may be prepared by compressing in a suitable machine, with the active compound being in a free-flowing form such as a powder or granules which is optionally mixed with a binder, disintegrant, lubricant, inert diluent, surface active agent or dispersing agent. Molded tablets comprised of a mixture of the powdered active compound with any suitable carrier may be made by molding in a suitable machine.

A syrup may be made by adding the active compound to a concentrated, aqueous solution of a sugar for example sucrose to which may also be added any accessory ingredient(s). Such accessory ingredient(s) may include flavourings, an agent to retard crystallization of the sugar or an agent to increase the solubility of any other ingredient, such as a polyhydric alcohol for example, glycerol or sorbitol, and suitable preservatives.

Formulations for rectal administration may be presented as a suppository with a usual carrier such as cocoa butter, or hydrogenated fats or hydrogenated fatty carboxylic acids.

Formulations suitable for parenteral administration conveniently comprise a sterile aqueous preparation of the active compound which is preferably isotonic with the blood of the recipient.

Nasal spray formulations comprise purified aqueous solutions of the active compound with preservative agents and isotonic agents. Such formulations are adjusted to a pH and isotonic state compatible with the nasal mucous membranes.

Ophthalmic formulations are prepared by a similar method to the nasal spray except the pH and isotonic factors are adjusted to match that of the eye.

Topical formulations comprise the active compound dissolved or suspended in media such as mineral oil, petrolatum, polyhydroxy alcohols or other bases used for topical pharmaceutical formulations. The addition of other accessory ingredients, vide infra, may be desirable.

In addition to the aforementioned ingredients, the formulations of this invention may further include one or more accessory ingredient(s) selected from diluents, buffers, flavouring agents, binders, disintegrants, surface active agents, thickeners, lubricants, preservatives (including antioxidants) and the like.

When used in medicine, the salts of the compound of formula (I) should be both pharmacologically and pharmaceutically acceptable, but non-pharmaceutically acceptable salts may conveniently be used to prepare the free active compound or pharmaceutically acceptable salts thereof and are not excluded from the scope of this invention. Such pharmacologically and pharmaceutically acceptable salts include, but are not limited to, those prepared from the following acids: hydrochloric, hydrobromic, sulphuric, nitric, phosphoric, maleic, salicylic, p-toluenesulfonic, tartaric, citric, methanesulphonic, formic, malonic, succinic, naphthalene-2-sulphonic and benzenesulphonic. Also pharmaceutically acceptable salts can be prepared as alkaline metal or alkaline earth metals, such as sodium, potassium or calcium salts of the carboxylic acid group. The esters may be, e.g., the methyl, ethyl, propyl, butyl, or isobutyl esters thereof.

The following Examples are provided by the way of illustration of the present invention and should in no way be construed as a limitation thereof. All temperatures indicated are in degrees Celsius.

EXAMPLE 1

(E)-3-{6-[3-pyrrolidino-1-(4-Trifluoromethylphenyl)-prop-1E-enyl]-2-pyridyl}acrylic acid 2-Bromo-6-(4-trifluoromethylbenzoyl)pyridine, m.p. 66°–68° C. (prepared by reacting 2,6-dibromopyridine and 4-trifluoromethylenzonitrile in dry ether in the presence of butyllithium) ethyl acrylate, triethylamine, palladium(II) acetate, triphenylphosphine and acetonitrile were heated at 150° C. in an autoclave with stirring for six hours to yield (E)-ethyl-3-[6-(4-trifluoromethylbenzoyl)-2-pyridyl]acrylate, m.p. 129°–132° C. Butyllithium was added under nitrogen to a stirred suspension of triphenyl-2-pyrrolidinoethylphosphonium bromide in dry toluene to form a Wittig reagent. After 0.5 hours, the acrylate compound prepared above, in toluene was added and the resulting suspension was heated at 75° C. with stirring for 2 hours. The cooled solution was diluted with ether and treated with hydrochloric acid (2M). The aqueous phase was separated, washed with ether, and basified with potassium carbonate (ice) and extracted with ether. The mixture of isomeric esters obtained by evaporation was dissolved in ethanol containing sodium hydroxide solution (1M) and partially evaporated on the steam bath under reduced pressure for 5 minutes. The residual aqueous solution was neutralized with sulfuric acid and evaporated to dryness.

The solid residue was extracted with hot isopropanol and the extracts were concentrated until crystallization commenced. The (E)-3-{6-[3-pyrrolidino-1-(4-Trifluoromethylphenyl)prop-1E-enyl]-2-pyridyl}acrylic acid after recrystallization from isopropanol, melted at m.p. 223°–225° C. (decomp).

EXAMPLE 2

Antihistaminic Activity

The longitudinal muscle was isolated from the intact ileum of guinea-pigs (Hartley, male 250–400 g) and placed in an organ bath under 300 mg tension. After one hour of equilibration, cumulative concentration-response curves (Van Rossum, J. M., *Arch. Int. Pharmacodyn. Ther.* 143, 299–330, 1963) in histamine were obtained. Following washing, the tissues were incubated for one hour with the test compound and then a second histamine concentration-response curve was run. Shifts to the right of the agonist concentration-response curve produced by the antagonists were used to construct Schild plots (Arunlakshana, O. and Schild, H. O., *Br. J. Pharmacol.* 14, 48–58, 1959). Regression of Log (dr-1) on Log [B], where dr is an equiactive response in the presence and absence of antagonist and [B1] is the molar concentration of antagonist, allowed an estimate of $pA_2$, i.e. the negative log of the concentration of antagonist which shifts the control histamine concentration-response curve 2X to the right.

TABLE I
Results of Antihistamine Assays

| Compound | $pA_2$ |
|---|---|
| Triprolidine | 10.1 |
| Compound of Formula (I) | 10.4 |

EXAMPLE 3

Formulations (A)-Injection

| Ingredient | Amount per ampoule |
|---|---|
| Compound of formula (I) | 1.0 mg |
| Water for injections, q.s. | 1.0 mL |

The finely ground active compound was dissolved in the water for injections. The solution was filtered and sterilized by autoclaving.

(B)-Suppository

| Ingredient | Amount per suppository |
|---|---|
| Compound of Formula (I) | 1.0 mg |
| Cocoa Butter, or Wecobee ™ Base q.s. | 2.0 g |

Wecobee is a trademark and is a hydrogenated fatty carboxylic acid.

The finely ground active compound was mixed with the melted suppository base (either Cocoa Butter or Wecobee TM base), poured into molds and allowed to cool to afford the desired suppositories.

(C)-Syrup

| Ingredient | Amount per 5 mL |
|---|---|
| Compound of Formula (I) | 1.0 mg |
| Ethanol | 0.3 mg |
| Sucrose | 2.0 mg |
| Methylparaben | 0.5 mg |
| Sodium Benzoate | 0.5 mg |
| Cherry Flavour | q.s. |
| Coloring | q.s. |
| Water | q.s. to 5.0 mL |

Ethanol, sucrose, sodium benzoate, methylparaben, and flavouring were combined in 70% of the total batch quantity of water. Coloring and the active compound were dissolved in the remaining water, then the two solutions were mixed and clarified by filtration.

(D)-Tablet

| Ingredient | Amount per Tablet |
|---|---|
| Compound of Formula (I) | 1.0 mg |
| Lactose | 110.0 mg |
| Corn Starch, Pregelatinized | 2.5 mg |
| Potato Starch | 12.0 mg |
| Magnesium stearate | 0.5 mg |

The active compound was finely ground and intimately mixed with the powdered excipients lactose, potato starch and magnesium stearate. The formulation was then compressed to afford a tablet weighing 126 mg.

(E)-Capsule

| Ingredient | Amount per Capsule |
|---|---|
| Compound of Formula (I) | 1.0 mg |
| Lactose | 440.0 mg |
| Magnesium Stearate | 5.0 |

The finely ground active compound was mixed with the powdered excipients lactose, corn starch and stearic acid and packed into two part, gelatin capsules.

(F)-Tablet

| Ingredient | Amount per Tablet |
|---|---|
| Compound of Formula (I) | 1.0 mg |
| Pseudoephedrine HCl | 60.0 mg |
| Lactose | 62.5 mg |
| Potato Starch | 14.0 mg |
| Magnesium Stearate | 1.0 mg |
| Gelatin | 2.8 mg |

A tablet was prepared from the above formulation by the method previously described in Example 3 (D).

(G)-Syrup

| Ingredient | Amount per 5 mL |
|---|---|
| Compound of Formula (I) | 1.0 mg |
| Pseudoephedrine HCl | 30.0 mg |
| Codeine Phosphate | 10.0 mg |
| Guaifenesin | 100 mg |
| Methylparaben | 0.5 mg |
| Sodium benzoate | 0.5 mg |
| Flavor | q.s. |
| Color | q.s. |
| Glycerol | 500 mg |
| Sucrose | 2000 mg |
| Purified Water | q.s. to 5.0 mL |

A syrup containing other active ingredients in addition to a compound of formula (I) was prepared from the above ingredients by an analogous method to that described for Example 3 (C) above.

| (H)-Nasal Spray | |
| --- | --- |
| Ingredient | Amount per 100.0 mL |
| Compound of Formula (I) | 1 g |
| Sodium Chloride | 0.8 g |
| Preservative | 0.5 g |
| Purified Water | q.s. 100.0 mL |

The preservative was dissolved in warm purified water and after cooling to 25°–30° C. the sodium chloride and the compound of formula (I) were added. The pH was then adjusted to 5.5–6.5 and purified water was added to bring the final volume to 100.0 mL.

| (I)-Ophthalmic Solution | |
| --- | --- |
| Ingredient | Amount per 100.0 mL |
| Compound of Formula (I) | 0.1 g |
| Sodium Chloride | 0.8 g |
| Preservative | 0.5 g |
| Water for injection | q.s. 100.0 mL |

This formulation was prepared in a similar way to the nasal spray.

| (J)-Topical Cream | |
| --- | --- |
| Ingredient | Amount per 100.0 mL |
| Compound of Formula (I) | 0.1 g |
| Emulsifying Wax, N.F. | 15.0 g |
| Mineral Oil | 5.0 g |

We claim:

1. A method of obtaining an antihistaminic effect in a human in need thereof comprising administering an effective antihistaminic amount of the compound of formula I

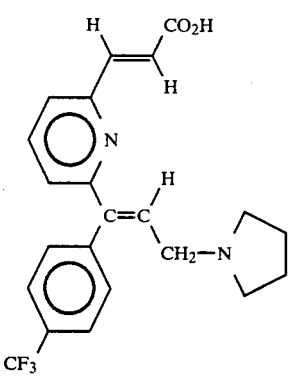

or a pharmaceutically acceptable salt thereof to said human.

2. The method of claim 1 in which the compound is administered.

3. The method of claim 1 in which the salt is administered.

4. A pharmaceutical composition for use as an antihistamine containing an effective antihistaminic amount of the compound of formula I

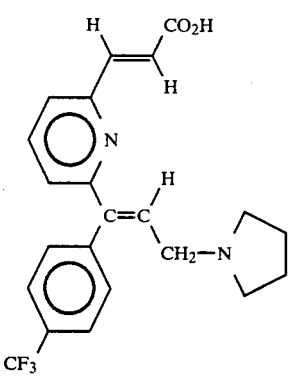

or a pharmaceutically acceptable salt thereof together with a pharmaceutically acceptable carrier therefor.

* * * * *